United States Patent [19]

Homsy

[11] Patent Number: 4,576,608

[45] Date of Patent: Mar. 18, 1986

[54] POROUS BODY-IMPLANTABLE POLYTETRAFLUOROETHYLENE

[76] Inventor: Charles A. Homsy, 11526 Raintree Cir., Houston, Tex. 77024

[21] Appl. No.: 549,805

[22] Filed: Nov. 8, 1983

Related U.S. Application Data

[63] Continuation-in-part of Ser. No. 204,528, Nov. 6, 1980, abandoned.

[51] Int. Cl.[4] .......................... A61F 2/02; A61F 2/08; A61F 2/30
[52] U.S. Cl. ........................................ 623/11; 623/13; 623/18; 128/92 C; 128/92 CA; 264/127; 428/422
[58] Field of Search ...................... 3/1, 1.9; 128/92 C, 128/92 CA; 428/422, 294; 264/127

[56] References Cited

U.S. PATENT DOCUMENTS

| | | | |
|---|---|---|---|
| 3,992,725 | 11/1976 | Homsy | 3/1 |
| 4,096,227 | 6/1978 | Gore | 264/127 |
| 4,118,532 | 10/1978 | Homsy | 428/294 |
| 4,127,902 | 12/1978 | Homsy | 3/1 |
| 4,129,470 | 12/1978 | Homsy | 156/155 |
| 4,347,204 | 8/1982 | Takagi et al. | 264/127 |
| 4,455,690 | 6/1984 | Homsy | 623/13 |

FOREIGN PATENT DOCUMENTS 051955  4/1985  European Pat. Off. .

*Primary Examiner*—Helen M. McCarthy
*Attorney, Agent, or Firm*—Vinson & Elkins

[57] ABSTRACT

A composition of matter, and the method of making same, suitable for in vivo implantation to provide an environment in which normal tissue growth is fostered, which composition is a porous, fibrous structure of polytetrafluoroethylene fibers and resin, wherein the combination is sintered at a temperature which fuses the fibers together without substantial detriment to their tensile strength. The composition is prepared containing a material which is soluble in a suitable solvent, which subsequent to sintering of the composition, may be removed to produce the desired amount of void space in the composition.

7 Claims, No Drawings

POROUS BODY-IMPLANTABLE POLYTETRAFLUOROETHYLENE

CROSS REFERENCE TO RELATED APPLICATIONS

This application is a continuation-in-part application of my prior copending application Ser. No. 204,528, filed Nov. 6, 1980, abandoned.

BACKGROUND OF THE INVENTION

1. Field of the Invention

The present invention relates to a porous, in vivo implantation material in which normal tissue growth is fostered. More particularly, the vivo implantation material is a sintered combination of polytetrafluoroethylene fibers and resin having void space of 50 to 90 percent.

2. Prior Art

The present inventor has developed a number of in vivo implantable materials utilizing polytetrafluoroethylene (PTFE) as a base resin. The PTFE resin is highly suitable for in vivo implantation due to its low incidence of rejection by the surrounding host tissue. However, in this field of research, it has been found that the intended site of in vivo implantation defines the form of material to be used. Thus, some applications require supple thin sheets having low Young's modulus of elasticity, some require tubes of high flexibility and flexural fatigue resistance, while others require rigid, solid blocks of material that can be machined or carved. In other words, the human body comprises bone and tissue arranged in such a manner that different mechanical parameters apply in virtually each possible application of an in vivo implantable material.

Consequently, there has been a continuous search for combinations of materials that can be utilized at specific sites in the body to accomplish a given set of tasks. Typical of one of these materials is the implantable material taught and claimed in U.S. Pat. No. 3,992,725, issued to the present inventor. Prior to that patent, there had not been a suitable, porous material providing for ingrowth of normal body tissues. However, the ingrowth material of that patent is usually black in color, due to the fibers used therein. In addition, the tensile stress behavior, abrasive resistance and flexural fatigue life of that material limits some of its potential uses.

Other work in this field is typified by U.S. Pat. No. 3,556,161, directed to PTFE resin sheets.

My prior U.S. Pat. No. 4,118,532 discloses a wear material suitable for in vivo implantation in which the material is processed to orient the fibers parallel to the surface.

The present invention, however, overcomes these and other deficiencies, as explained more completely hereinafter.

SUMMARY OF THE INVENTION

The present invention is directed to a composition of matter suitable for in vivo implantation prepared by the process which comprises blending together polytetrafluoroethylene (PTFE) resin, PTFE fibers and from about 50 to about 90 percent by volume of material which is soluble in a non-solvent for said PTFE; forming a mat from said blend; compacting said mat; sintering said compacted mat at a temperature which fuses said PTFE fibers into a continuous matrix; and subsequently removing from said sintered, compacted mat substantially all of said material which is soluble in a non-solvent for said PTFE. The composition of the present invention has a porosity of from about 50 to about 90 percent by volume; a tensile strength of from 20 to about 300 Kg per $cm^2$; and for porosity above 75 percent has a substantial portion thereof with a varying elastic modulus (Young's modulus). The major proportion of the pores, in the composition of the invention, have a pore size distribution of between about 80 to about 400 micra.

In addition, there is also provided a laminated material consisting of a first and second layer, the first layer comprises the implantable material described and claimed in U.S. Pat. No. 3,992,725; and the second layer comprises the composition of the present invention.

It is an object of this invention to provide an improved material for in vivo implantation.

A further object of this invention is to provide a material for in vivo implantation which is of lighter color than other materials which promote ingrowth of body tissue.

Another object of the invention is to provide a material for in vivo implantation having an improved abrasion resistance and flexural fatigue life.

Another object of the invention is to provide a laminate of material suitable for in vivo implantation.

Still another object of the invention is to provide a material or laminate of porous PTFE compositions, the overall properties of which provide a substantial portion thereof with a varying elastic modulus (Young's modulus) as defined from a conventional stress-strain curve.

DESCRIPTION OF THE PREFERRED EMBODIMENTS

The present invention is directed to a porous, in vivo implantable polytetrafluoroethylene (PTFE) material, prepared from a combination of PTFE resin and fibers. The PTFE material has been used for implantable devices and has been found to be bio-compatible, that is, it does not produce any inflammatory response by the host tissue. The preferred material to be used is marketed by DuPont Co. as Teflon TFE.

It has been unexpectedly found that structures of PTFE prepared according to the methods of this invention compensate for the relatively low surface energy of PTFE polymer by providing a pore structure of irregular geometry and enormous surface area. Apparently, the ability of cells to attach and move within the porous structures of this invention is greatly enhanced by the geometry of this structure which derives from a combination of polymer fibrous elements and polymer nodal elements. The present material, however, does not have the ingrowth potential of the material claimed in U.S. Pat. No. 3,992,725 because it exhibits a lower surface energy than achieved with the latter material. However, laminates of the present invention with that ingrowth material are part of the present invention.

The preferred composition of material of the present invention is made by intimately mixing in the proportions hereinafter set forth PTFE fibers and PTFE resin. The ratio of PTFE fiber to resin is preferred to be 1 to 1 for 80% porous structures; this ratio is preferred to be greater than 1 to 1 for less porous structures, e.g., increasing to 2.3 to 1 for 50% porous structures. The PTFE fibers are preferred to have a strand length up to 2 inches.

In order to help provide the desired void space, a material which is soluble in a suitable solvent, but which is not a solvent for the PTFE, is added to the above mixture in an amount to produce the desired amount of void space in the material, preferably in the range from 50% to 90% of the volume of the finished material. If water is to be the solvent, the soluble material may be common material such as sodium chloride crystals of particle size between 10 and 500 microns.

Alternatively other soluble material/solvent combinations may be used. For example, when water is to be the solvent, soluble materials may be selected from the group of water soluble salts which are thermally stable at temperatures below about 700° F. Such salts could be sodium carbonate, calcium fluoride, magnesium sulphate, and others. It will generally be preferred to use the sodium chloride-water system since the sodium chloride would be completely compatible in the body in the event small amounts were left in the material from the leaching step hereinafter described.

A typical formulation would include 80% sodium chloride, 10% PTFE resin fibers and 10% PTFE particulate resin. Such formulation when prepared as herein set forth has been found to have moderate tissue ingrowth, sufficient strength and sufficient flexural properties. Table I shows the preferred range of components.

TABLE I

| PTFE resin fibers | 2.5% to 35% by volume |
| PTFE resin particles | 2.5% to 25% by volume |
| soluble material | 90% to 50% by volume |

The steps involved in preparing these materials are as follows:

a. Mixing: In this step the PTFE polymer resin, PTFE fibers and soluble ingredients are suspended in a suitable organic solvent such as purified isoparaffinic solvent; it is preferred that aromatic content of such solvent be less than 1% by weight; the resulting slurry is mixed at very high speed in a high shear mixer such as a Waring blender. The proportion of solvent to dry ingredients is important and must be adjusted to the size of the mixer used. The total volume of our mixer is 1000 milliliters and 500 milliliters of solvent are used for dry ingredient weights of the order of 80 grams. Mixing is carried out for between one and five minutes depending upon the particular ingredients used. The fibers are appproximately ¼ to ⅜ inch long.

b. Filtration: The mixed slurry is rapidly poured into a vacuum filter such a Buchner funnel, and filtration proceeds from between a few seconds to several minutes depending upon ingredients used. The residual solvent left in the filter cake is carefully monitored so as to be less than about 20% by weight.

c. Compression: The filter cake from step (b) is placed within the platens of a heated press (100° to 200° F.) and compression is applied at levels of between 50 to 1,500 pounds per square inch for between one and five minutes, again depending upon the particular ingredients. The present residual solvent in the filter cake after compression is routinely monitored and conditions are adjusted so that the level of solvent is between six and twenty weight percent.

d. Rolling: The compressed filter cake from step (c) is run through the nip of heated rolls such that the thickness of the cake is reduced in decrements of approximately 20/1000 of an inch to levels of between 80 and 20/1000 of an inch depending upon the intended final thickness of the product. The temperature of the heated rolls should be in the range of 100° F. through 280° F. That is, heated rolls over this temperature range are required in order to help volatilize the carrier solvent. Moreover, during this step each pass through the rolls is made perpendicular with the direction of the previous rolling maneuver.

e. Drying: Stock material is dried to evaporate any residual solvent by placing in an oven held at temperatures of between 150° F. and 350° F. for several hours—up to 48 hours usually.

f. Sintering: The dried stock is now sintered. Sintering is carried out in a heated press at temperatures between 625° F. and 680° F. and a pressure between 500 to 750 pounds per square inch (lbs/in$^2$) for periods of time from 4 to 15 minutes, or more, depending upon the thickness of the material being sintered. The mats are usually about 1 to 2 mm thick prior to sintering. In order to prepare material of varying thickness, a plurality of 1 to 2 mm mats are stacked, and then sintered. Sintering time depends upon the number of layers of mats and temperature, at a given pressure. The preferred pressure is from 550 to 675 lbs/in$^2$, and most preferably at 625 lbs/in$^2$, the best temperature for sintering is about 650° F., for the times shown in TABLE II, below:

TABLE II

| Sintering Times, at 650° F. | |
|---|---|
| Material Thickness, mm | Time, minutes |
| 1-2 | 4-6 |
| 3 | 8 |
| 4 | 9 |
| 5 | 10 |
| 6-10 | 15 |

With two or more layers and with thickness greater than 1 mm, the preferred pressure will be approximately one-half the above stated pressure.

g. Leaching: The stock is leached to dissolve out water soluble filler material by placement in a container containing distilled water and thereby develop discrete volume and porosity. Distilled water may be caused to flow at a slow rate through such container in order to provide the maximum driving force for diffusion of dissolved filler from the stock in a leaching water. The leaching step is usually allowed to proceed for 48 hours for stock having at thickness of 5 mm–10 mm. Longer times would probably be required for thicker stock. The distilled water is preferred to be warm to increase the rate of dissolving of salt.

h. Drying: The leach stock is then placed in an oven held at a temperature between about 160° F. and 350° F. in order to affect drying of the residual water contained within the stock material. The drying step may include a 24 hour hold at 300° F. to volatilize any residual solvent.

The product material from the above series of steps exhibits several important properties of significance to tissue ingrowth. During the leaching step the voids are created in the material. A portion of the voids have a nodal shape as they are formed by the leaching of generally spheroidal sodium chloride crystals from the material. In addition, the material which is produced as described also develops dendritic voids which interconnect in random fashion with the spheroidal voids to thereby provide a particularly effective open structure for the ingrowth of cellular elements which develop and mature fibrous tissue within the voids. The material also does not have its fibers positioned in parallel relation to the surface. However, the surface free energy of the material and specific surface area are lower than in the material of U.S. Pat. No. 3,992,725. As a result, a higher percentage of ingrowth occurs in the latter material than in the present. For some applications it is advisable to use a combination of materials having a first layer of the material of U.S. Pat. No. 3,992,725 and a fused layer of the all-PTFE material of this invention. This is particularly true where the combination material is to be used close to the skin, of a person of light complexion. The material of the present invention is essentially a white color.

It is believed that with the development and maturation of tissue within such voids, such tissue is not as vulnerable to infection as prior implants since substantial blood supply is developed to allow the normal body functions for fighting infection to be active within such material. In prior materials for implants, the appearance of an infection in connection with an implanted device generally necessitated the removal of the device if the normal body infection fighting mechanisms were not able to reach the infected area.

Additionally, because of the resiliency and distensibility of this composition of material, the tissues developing therein feel or are subjected to the normal mechanical forces at the sites of the implant which assist in the formation of the type of tissue needed at such location.

Upon consideration of the promotion into the composition of material of ingrowth of body tissues, such composition of material appears to have varied applications in all parts of the body, e.g., soft tissue augmentation, partial and complete joint prostheses, birth control by vas or tube blockage from material implant, fixation of artificial teeth, tendon and ligament replacement and fixation, alveolar ridge augmentation and other implant procedures.

It has been found that the kind and porosity of the composition of material may be controlled by the amount of soluble filler included in the original mixture.

In the formation of the material the rolling proceeds until the thickness of the material is of the order of one to two millimeters (mm) thick to thereby provide a maximum strength. When thicker stock is desired particularly for soft tissue and alveolar ridge augmentation it can be achieved by following the above steps (a), (b), (c), (d) and (e) and then stacking the dried stock to the desired multiple of the single ply thickness. The stacked layers are sandwiched between aluminum foil and placed within the platens of a press held at a temperature of 625° to 680° F. Pressure is applied gradually depending on the area of the laminate to a final hold pressure of about 625 pounds per square inch. This hold pressure is maintained for a period of time as set out above and may not need to exceed fifteen minutes. This laminated stock is then leached and dried as set forth in steps (g) and (h) above.

When the mat has been compacted, sintering should preferably be done under conditions which allow the resin to gel and fuse the fibers together without substantially diminishing the higher tensile strength of the fibers. The tensile strength of the PTFE fibers, above, is approximately 10 times that of the PTFE resin alone.

Subsequent removal from the sintered, compacted mat of essentially all of the material which is soluble in a non-solvent for the PTFE results in a flexible material whose strength is substantially greater than that to be expected for PTFE resins.

Although the published gelation temperature for PTFE fibers is given as that of the resin, it has been unexpectedly found that under the conditions of preparation of this invention, gelation of resin which fuses the fibers into a continuous matrix does not impair the fibrous quality of the fibers themselves.

The preferred ingredients, useful in preparing the compositions of the present invention, are bleached fibers of TEFLON TFE and TEFLON TFE-6 resin, sold by DuPont Company. The sodium chloride, reagent grade crystals, was supplied by J. T. Baker Laboratory Chemicals, but may be any equivalent grade supplied in the industry.

In preparing the all-TFE mats, there is mixed together the PTFE resin and fibers in a volume ratio between 1:5 and 10:1. The preferred composition for 80% porous structures has a ratio of resin to fiber of 1:1. This particular formulation is a relatively high strength, but exceedingly porous, material exhibiting ultimate tensile strength of the order of 40 kg/cm$^2$ and at the same time, providing essentially no region of constant elastic modulus (Young's modulus) as defined from the conventional stress-strain curve. That is, the all-TFE compositions are implant materials providing the low modulus advantage in not injuring ingrowth tissue. This is especially important with an all-TFE composition where the rate of ingrowth is lower than that observed with the carbon fiber/PTFE composition of U.S. Pat. No. 3,992,725.

The all-TFE compositions of the present invention can be laminated to suitable metallic or other substrates which will withstand temperatures of fusion bonding using the bonding methods described fully in U.S. Pat. No. 3,992,725. That is, by using as a bonding substrate a thin layer of fluorinated ethylenepropylene (such as solid by DuPont Company under the name TEFLON FEP). Particularly suitable are laminations of the present invention to bio-compatible fabric such as polyamide, polyaramid, polyimide or polyester fabric. This, also, may be accomplished by the method of using the TEFLON FEP resin, described above. U.S. Pat. No. 3,992,725 is incorporated herein by reference for the purpose of illustrating methods of bonding the present composition to substrates and orthopedic devices. Silicone rubber also may be used to form a lamination with the porous material of the present invention. Such lamination may be accomplished by any suitable method. As disclosed in my application for patent, executed concurrently with the parent application of this application filed Nov. 6, 1980 and assigned Ser. No. 204,529, U.S. Pat. No. 4,455,690 dipping or spray coating with a dispersion of medical grade silicone rubber in a non-polar vehicle provides a tenaciously bound coating on the porous material. Laminations of silicone rubber and the porous material of this invention are useful in sealing surface porosity and in bonding the porous material to other materials.

What is claimed is:

1. A composite in vivo implantation material comprising:
    a porous, compacted, sintered blend of biocompatible resin fibers and a biocompatible resin binder, said resin fibers consisting entirely of polytetrafluoroethylene fibers and said resin binder consisting entirely of particles of polytetrafluoroethylene resin, said resin fibers and said resin binder being fused together to form a continuous porous matrix with said resin binder retaining said resin fibers therein, said material having a porosity between around fifty (50) percent to ninety (90) percent by volume, the majority of the pores in said porous sintered blend having a size in the range between eighty (80) and four hundred (400) microns.

2. The composite material as set forth in claim 1 further characterized in that the ratio by volume of resin fibers to resin binder in said blend is in the range from about 1 to around 2.3 to 1.

3. The composite material as set forth in claim 1 further characterized in that said resin fibers are in random position therein;
and a substantial portion of said resin fibers have a strand length between around one-fourth (¼) and around three-eighths (⅜) of an inch.

4. The composite material as set forth in claim 1 wherein said resin fibers are in random position therein; and said porous composite material is constructed and arranged so that a substantial portion thereof has a variable elastic modulus (Young's modulus) as defined from a conventional stress-strain curve.

5. A laminated material suitable for in vivo implantation and having at least two layers, one of said layers comprising:

a porous compacted, sintered blend of a biocompatible fiber component and a biocompatible binder component, said fiber component consisting entirely of polytetrafluoroethylene fibers and said binder component consisting entirely of particles of polytetrafluoroethylene resin, said components being fused together to form a continuous porous matrix with said polytetrafluoroethylene resin retaining said polytetrafluoroethylene fibers therein, said porous sintered blend having a porosity between around fifty (50) percent to ninety (90) percent by volume, the majority of the pores in said porous sintered blend having a size in the range between eighty (80) and four hundred (400) microns; and the other layer being formed of a suitable biocompatible material and secured to said one layer to form the laminated material.

6. The laminated material as set forth in claim 5 further characterized in that the other layer comprises a fused blend of polytetrafluoroethylene fibers and carbon fibers bonded with a biocompatible polytetrafluoroethylene resin.

7. A laminated material as set forth in claim 5 wherein the other layer thereof is comprised of a biocompatible silicone rubber and said layers are bonded together.

* * * * *